(12) United States Patent
Rowland

(10) Patent No.: US 7,867,524 B2
(45) Date of Patent: Jan. 11, 2011

(54) ENERGIZING FORMULATION

(76) Inventor: David Rowland, 985 Route 540, Woodstock, NB (CA) E7M 6B7

( * ) Notice: Subject to any disclaimer, the term of this patent is extended or adjusted under 35 U.S.C. 154(b) by 80 days.

(21) Appl. No.: 12/241,711

(22) Filed: Sep. 30, 2008

(65) Prior Publication Data

US 2009/0104290 A1 Apr. 23, 2009

Related U.S. Application Data

(60) Provisional application No. 60/977,670, filed on Oct. 5, 2007.

(51) Int. Cl.
- *A61K 36/815* (2006.01)
- *A61K 36/704* (2006.01)
- *A61K 36/00* (2006.01)

(52) U.S. Cl. ...................... 424/725; 424/773

(58) Field of Classification Search ............... None
See application file for complete search history.

(56) References Cited

U.S. PATENT DOCUMENTS

| | | | |
|---|---|---|---|
| 5,958,417 A * | 9/1999 | Hsu | 424/764 |
| 6,693,129 B2 * | 2/2004 | Rath | 514/474 |
| 7,008,663 B2 * | 3/2006 | Jung et al. | 426/623 |
| 7,179,488 B2 | 2/2007 | Sherwood et al. | |
| 2002/0068095 A1 * | 6/2002 | Qi et al. | 424/725 |
| 2003/0078214 A1 * | 4/2003 | Kelly | 514/27 |
| 2003/0206978 A1 | 11/2003 | Sherwood et al. | |
| 2005/0238654 A1 | 10/2005 | Takeda | |
| 2006/0239928 A1 | 10/2006 | Hei et al. | |

FOREIGN PATENT DOCUMENTS

| | | | |
|---|---|---|---|
| CN | 1094582 A | * | 11/1994 |
| JP | 06327434 A | * | 11/1994 |
| WO | WO 01/22934 | | 4/2001 |
| WO | WO 03/086267 | | 10/2003 |
| WO | WO03086267 | | 10/2003 |

OTHER PUBLICATIONS

Man, CK, "The antioxidative effect of Lycium fruit extract on hyperglycemia-induced oxidative stress in human liver and rat muscle cell lines". Thesis Abstract, University of Hong Kong, Aug. 2005.

* cited by examiner

*Primary Examiner*—Patricia Leith
(74) *Attorney, Agent, or Firm*—Bereskin & Parr LLP/S E N. C.R.L., srl

(57) ABSTRACT

The present invention relates to a pre-mix and a pharmaceutical composition for oxygenating a subject's tissues, uses and methods of treatment thereof.

12 Claims, 17 Drawing Sheets

ENERGIZING FORMULATION

BACKGROUND OF THE INVENTION (a) Field of the Invention

The present invention relates to a pre-mix and pharmaceutical composition for oxygenating a subject's tissues, methods of preparation of such, as well as uses and methods of treatment thereof.

(b) Description of Prior Art

International Publication No. WO 2001/22934 entitled "Delivery of small doses of ingestible treatments" relates to the treatment of human or animal diseases, illnesses, and conditions that may be effectively practiced by administrating extremely small dosages of bioactive substance, which cause a "trigger effect". By neurostimulating the human's or animal's brain, one effects a positive physical manifestation by substantially solely influencing the human's or animal's gustatory, or gustatory and olfactory, receptors. This is typically accomplished using a delivery vehicle containing only between about 8 micrograms and 0.5 picograms of the bioactive substance. Various bioactive substances are listed in this International Publication such as Goji fruit (*lycium barbarum*) and Red Clover blossoms (*trifolium pratense*). However, there are no teachings or suggestions of a composition of Goji fruit (*lycium barbarum*) and Red Clover blossoms (*trifolium pratense*) exclusively or in combination with other components.

United States Patent Application No. 2005/0238654 entitled "Compositions and methods for weight loss" discloses dietary supplements and methods for management and control of body weight containing at least one liver protecting agent and at least one mushroom in the form of powder, extract, or combinations thereof. There is disclosed a list of possible liver protecting agents to be incorporated in the dietary supplement which includes both Goji fruit (*lycium barbarum*) and Fo Ti (radix *polygonum multiflorum*). However, there are no teachings or suggestions of a composition comprising Goji fruit (*lycium barbarum*) and Fo Ti (radix *polygonum multiflorum*) exclusively or in combination with other components.

U.S. Pat. No. 7,179,488 entitled "Process for co-spray drying liquid herbal extracts with dry silicified MCC" discloses a process for preparing dry extracts from a liquid extract and at least one additional substance by a spray-drying process, characterized in that the at least one additional substance is added to the spray-drying process in a dry form during the spray-drying processes. Various herbal extracts can be submitted to this technology such as Red Clover blossoms (*trifolium pratense*) and Fo Ti (radix *polygonum multiflorum*). However, there are no teachings or suggestions of a composition containing Red Clover blossoms (*trifolium pratense*) and Fo Ti (radix *polygonum multiflorum*) exclusively or in combination with other components.

United States Publication No. 2003/0206978 entitled "Agglomerated particles including an active agent coprocessed with silicified microcrystalline cellulose" discloses a solid dosage form which includes an active agent and silicified microcrystalline cellulose, the dosage form being formed by a) combining a wetted active agent with dry silicified microcrystalline cellulose in a dryer to form agglomerated particles; and b) incorporating the agglomerated particles into the solid dosage form. It is disclosed that step b) can consists of a step of combining said silicified microcrystalline cellulose, said active agent, and colloidal silicon dioxide in a dryer. Preferably, the dryer is a spray dryer, and, in certain embodiments, the active agent consists of an herbal extract such as Red Clover blossoms (*trifolium pratense*) and Fo Ti (radix *polygonum multiflorum*). However, there are no teachings or suggestions of a composition containing Red Clover blossoms (*trifolium pratense*) and Fo Ti (radix *polygonum multiflorum*) exclusively or in combination with other components.

United States Publication No. 2006/0239928 entitled "Transmucosal administration of drug compositions for treating and preventing disorders in animals" relates to compositions for transmucosal administration to an animal containing at least one active agent and a pharmaceutically acceptable carrier. The active agent can be chosen from nutraceuticals that can include micronutrients such as vitamins and minerals, dietary supplements, amino acids, herbs, antioxidants, tribal medicines, prebiotics, probiotics, macrobiotics and nutritional supplements. Possible examples of those nutraceuticals are Red Clover blossoms (*trifolium pratense*) and Fo Ti (radix *polygonum multiflorum*). However, there are no teachings or suggestions of a composition containing Red Clover blossoms (*trifolium pratense*) and Fo Ti (radix *polygonum multiflorum*) exclusively or in combination with other components.

International Publication Number WO 2003/086267 entitled "Mutli-phase, multi-compartment capsular system" relates to a multi-compartment capsule, containing a first receiving chamber containing at least one ingredient having a first physical state, this ingredient being selected from the group consisting of a nutraceutical, a vitamin, a dietary supplement and a mineral, and a second receiving chamber containing at least one ingredient having a second physical state, this second ingredient being selected from the group consisting of a nutraceutical, a vitamin, a dietary supplement and a mineral. Furthermore, the first physical state of the ingredient of the first receiving chamber is different from the second physical state of the ingredient of the second receiving chamber and the ingredient of the first receiving chamber is different from the ingredient of the second receiving chamber. The nutraceutical, vitamin, dietary supplement or mineral ingredient to be integrated in either one of the chambers can be Fo Ti (radix *polygonum multiflorum*) in a preferred embodiment. However, there are no teachings or suggestions of a composition containing Fo Ti (radix *polygonum multiflorum*) exclusively or in combination with other components.

Thus, there remains a need for an effective means to combine the inherent properties of dried Goji fruit (*lycium barbarum*), dried Red Clover blossoms (*trifolium pratense*) and dried Fo Ti (radix *polygonum multiflorum*) altogether. Indeed, it would be highly unpredicted to be provided with a composition comprising an effective amount of each of these compounds for oxygenating a subject's tissues and therefore improving its health.

SUMMARY OF THE INVENTION

In accordance with the present invention there is provided a pre-mix and related pharmaceutical composition for oxygenating a subject's tissues, methods of preparation of such, as well as uses and methods of treatment thereof.

In accordance with one embodiment of the present invention, there is provided a premix for the preparation of a pharmaceutical composition for oxygenating a subject's tissues comprising:

a) Dried Goji fruit (*lycium barbarum*) 20 to 60% by weight
b) Dried Red Clover blossoms (*trifolium* 10 to 50% by weight pratense)

c) Dried Fo Ti (radix *polygonum multiflorum*) 5 to 35% by weight

The premix may further comprise with respect to the total weight of a), b) and c), from 3 to 30% by weight of a glycine precursor.

The glycine precursor may be Di-Methyl Glycine, Tri-Methyl Glycine and Magnesium Glycinate.

The premix may further comprise with respect to the total weight of a), b) and c), from 1 to 10% by weight of a organogermanium oxide.

The organogermanium oxide may be beta-carboxyethylgermanium sesquioxide, beta-(alpha-methyl) carboxyethyl-germanium sesquioxide and di-(beta-carboxyethyl) germanium hydroxide.

The premix may further comprise with respect to the total weight of a), b) and c), from 3 to 30% by weight of a glycine precursor and from 1 to 10% by weight of an organogermanium oxide, where the glycine precursor may be Di-Methyl Glycine, Tri-Methyl Glycine and Magnesium Glycinate, and the organogermanium oxide may be beta-carboxyethylgermanium sesquioxide, beta-(alpha-methyl) carboxyethylgermanium sesquioxide and di-(beta-carboxyethyl) germanium hydroxide.

In accordance with one embodiment of the present invention, there is provided a pharmaceutical composition for oxygenating a subject's tissues comprising:
from 40% to 90% by weight of a premix comprising:
a) Dried Goji fruit (*lycium barbarum*) 20 to 60% by weight
b) Dried Red Clover blossoms (*trifolium pratense*) 10 to 50% by weight
c) Dried Fo Ti (radix *polygonum multiflorum*) 5 to 35% by weight in combination with from 10% to 60% by weight of a pharmaceutically acceptable carrier.

The premix of the pharmaceutical composition may further comprise with respect to the total weight of a), b) and c), from 3 to 30% by weight of a glycine precursor.

The glycine precursor may be Di-Methyl Glycine, Tri-Methyl Glycine and Magnesium Glycinate.

The premix of the pharmaceutical composition may further comprise with respect to the total weight of a), b) and c), from 1 to 10% by weight of an organogermanium oxide.

The organogermanium oxide compound may be beta-carboxyethylgermanium sesquioxide, beta-(alpha-methyl) carboxyethylgermanium sesquioxide and di-(beta-carboxyethyl) germanium hydroxide.

The premix of the pharmaceutical composition may further comprise with respect to the total weight of a), b) and c), from 3 to 30% by weight of a glycine precursor and from 1 to 10% by weight of an organogermanium oxide, where the glycine precursor may be Di-Methyl Glycine, Tri-Methyl Glycine and Magnesium Glycinate, and the organogermanium oxide compound may be beta-carboxyethylgermanium sesquioxide, beta-(alpha-methyl) carboxyethylgermanium sesquioxide and di-(beta-carboxyethyl) germanium hydroxide.

The pharmaceutically acceptable carrier may be polyethylene glycol, propylene glycol, propylene glycol monocaprylate, water and mixtures thereof.

The pharmaceutically acceptable carrier allows formulation of the composition as a liquid formulation, a soft-gel capsule, an enteric-coated soft-gel capsule, a capsule or an enteric capsule.

The pharmaceutically acceptable carrier may be sodium lauryl sulfate, hydroxypropyl methylcellulose, methylcellulose, hydroxypropylcellulose, hydroxyethylcellulose, polyvinylpyrrolidone, carboxymethylcellulose, polyethylene glycol, polyethylene oxide, polyvinyl alcohols, pregelatinised starch, lactose, mannitol, sucrose, sorbitol, xilitol, polyols, low molecular weights hydroxypropyl methycellulose, low molecular weights, low molecular weight polyvinylpyrrolidone, ionic and non-ionic surfactants, polyoxyalkylene derivatives of propylene glycol, organic acids, buffering agents, starch, fillers, lubricants, superdisintegrants, calcium carbonate, calcium phosphate, microcrystalline cellulose, hydrogenated castor oil, glyceryl palmitostearate, talc, stearic acid, vegetable stearate, silica, cross-carmelose sodium and mixtures thereof.

The pharmaceutically acceptable carrier allows formulation of the composition as a pill, a caplet, an enteric-coated caplet, a tablet, an enteric-coated caplet, a lozenge or an enteric-coated lozenge.

In accordance with one embodiment of the present invention, there is provided a method for preparing a pharmaceutical composition for oxygenating a subject's tissues comprising the step of mixing from 40% to 90% by weight of the premix of the present invention with from 10% to 60% by weight of a pharmaceutically acceptable carrier.

In accordance with one embodiment of the present invention, there is provided a method for improving health in a subject comprising the step of administering to the subject an effective amount of the pharmaceutical composition of the present invention.

The administration of the pharmaceutical composition is oral.

In accordance with one embodiment of the present invention, there is provided the use of the pharmaceutical composition of the present invention for improving health in a subject.

All references referred herein are hereby incorporated by reference.

BRIEF DESCRIPTION OF THE DRAWINGS

FIG. 1A illustrates the condition of the red blood cells of Subject male 1 before start of the study.

DETAILED DESCRIPTION OF THE INVENTION

In accordance with the present invention, there is provided a pre-mix and pharmaceutical composition for oxygenating a subject's tissues, methods of preparation of such, as well as uses and methods of treatment thereof.

The present invention will be more readily understood by referring to the following examples which are given to illustrate the invention rather than to limit its scope.

EXAMPLE 1

Preparation of the Pharmaceutical Composition. The Pharmaceutical composition was prepared by mixing from 40% to 90% by weight of a premix comprising from 20 to 60% by weight of Dried Goji fruit (*lycium barbarum*), from 10 to 50% of Dried Red Clover blossoms (*trifolium pratense*), from 5 to 35% by weight of Dried Fo Ti (radix *polygonum multiflorum*), from 3 to 30% by weight of Tri-Methyl Glycine and from 1 to 10% by weight of Germanium Sesquioxide, in combination with from 10% to 60% by weight of excipients. The pharmaceutical composition was formulated as a tablet.

Posology. Subjects were administered 5 tablets a day as follows: 2 tablets with breakfast, 2 tablets with lunch and 1 tablet with supper. The subjects were advised not to alter in any other way their regular diet for the time of the treatment. The treatment was carried out on a 30 days basis.

Figure 2:
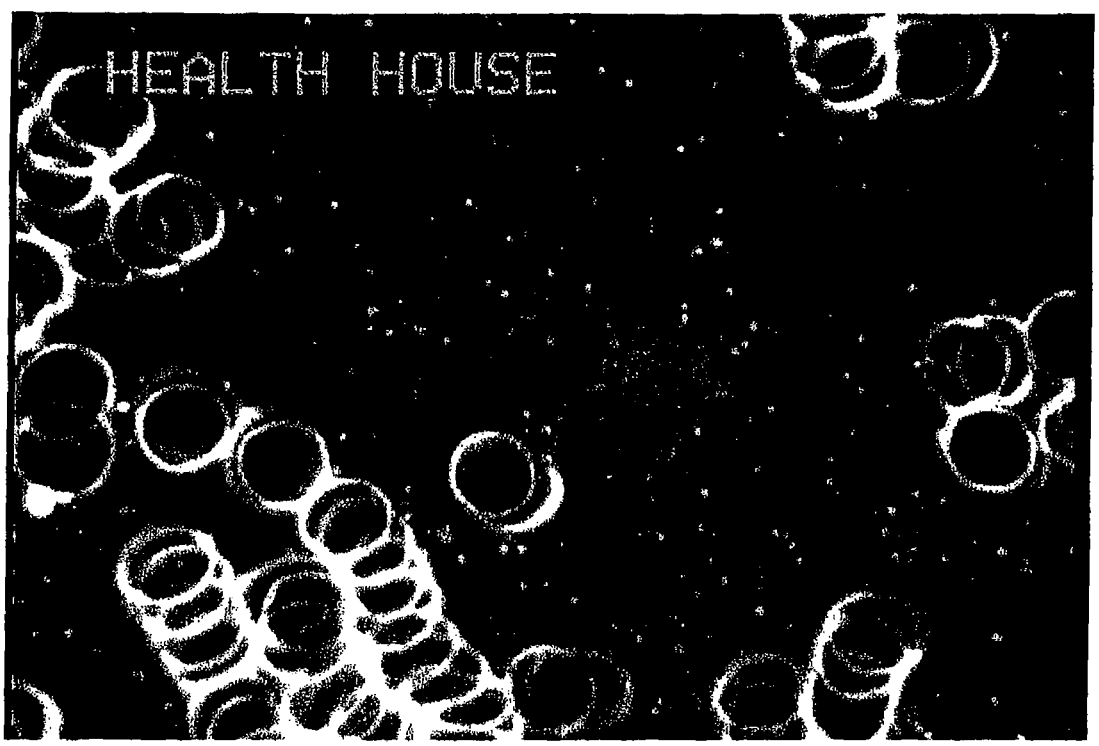
FIG. 2A illustrates the condition of the red blood cells of Subject 2 before start of study.
FIG. 2B illustrates the condition of the red blood cells of Subject 2 after administration of a pharmaceutical composition of Example 1.
Figure 2:
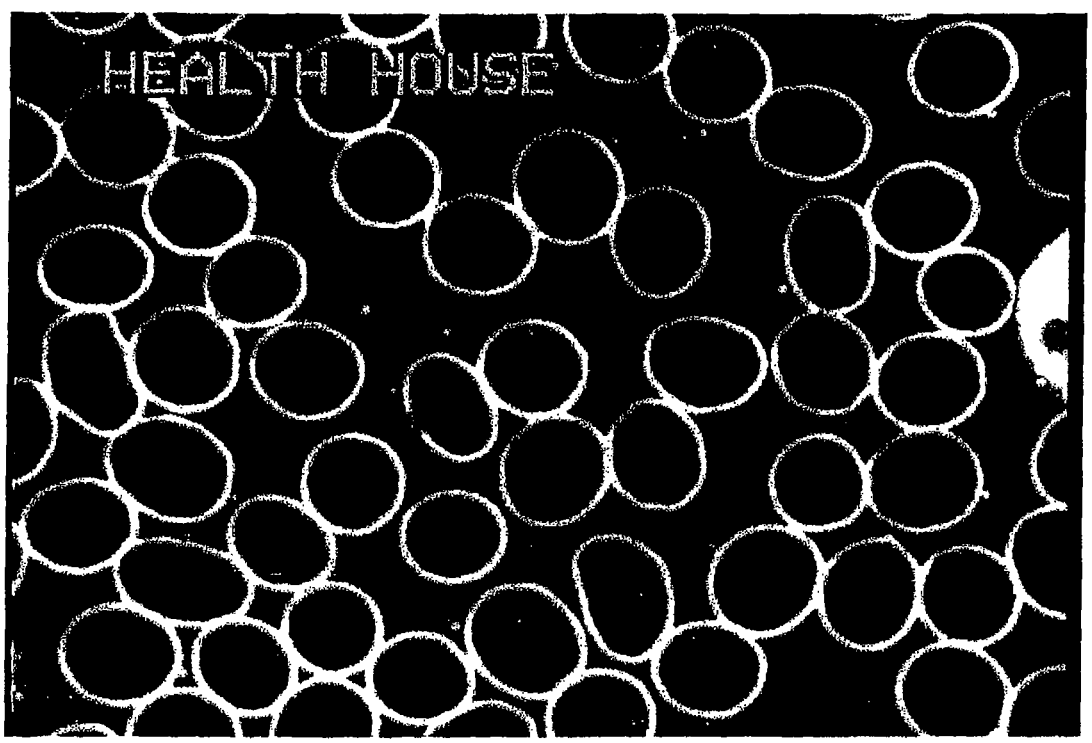
Figure 3:
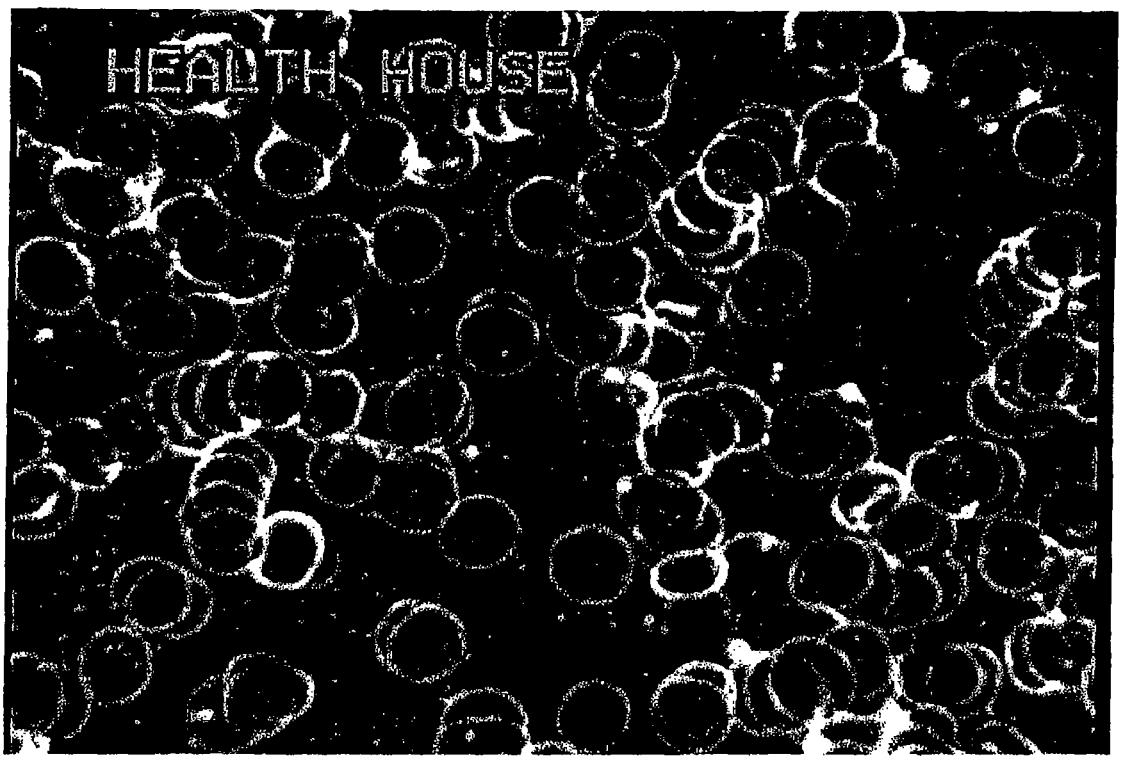
FIG. 3A illustrates the condition of the red blood cells of Subject 3 before start of study.
FIG. 3B illustrates the condition of the red blood cells of Subject 3 after administration of a pharmaceutical composition of Example 1.
Figure 3:
Figure 4A:
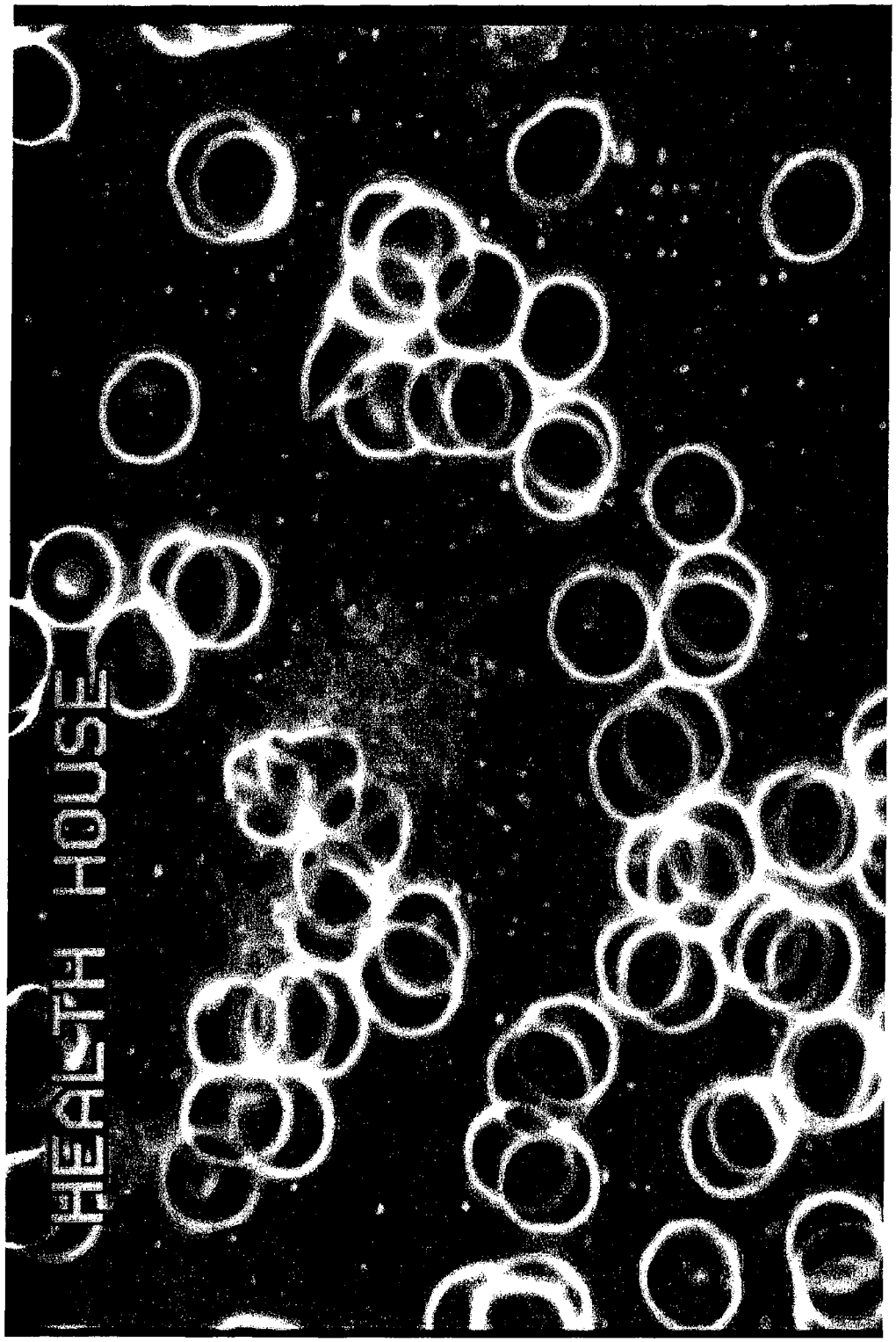
FIG. 4A illustrates the condition of the red blood cells of Subject male 1 after 22 days of administration of product Y.
Figure 4B:
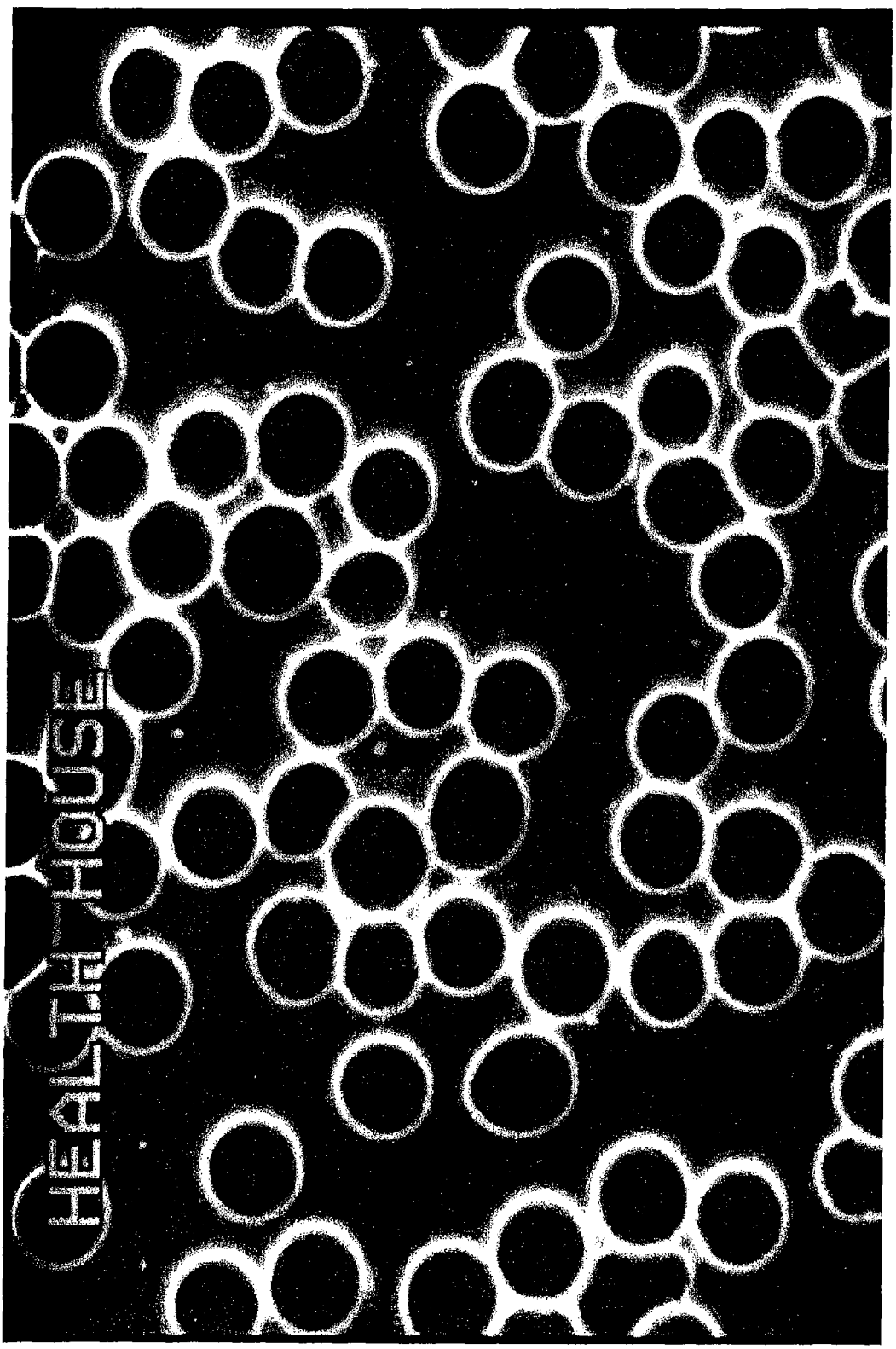
FIG. 4B illustrates the condition of the red blood cells of Subject male 1 after subsequent 22 days of administration of the pharmaceutical composition of Example 1.
Figure 5A:
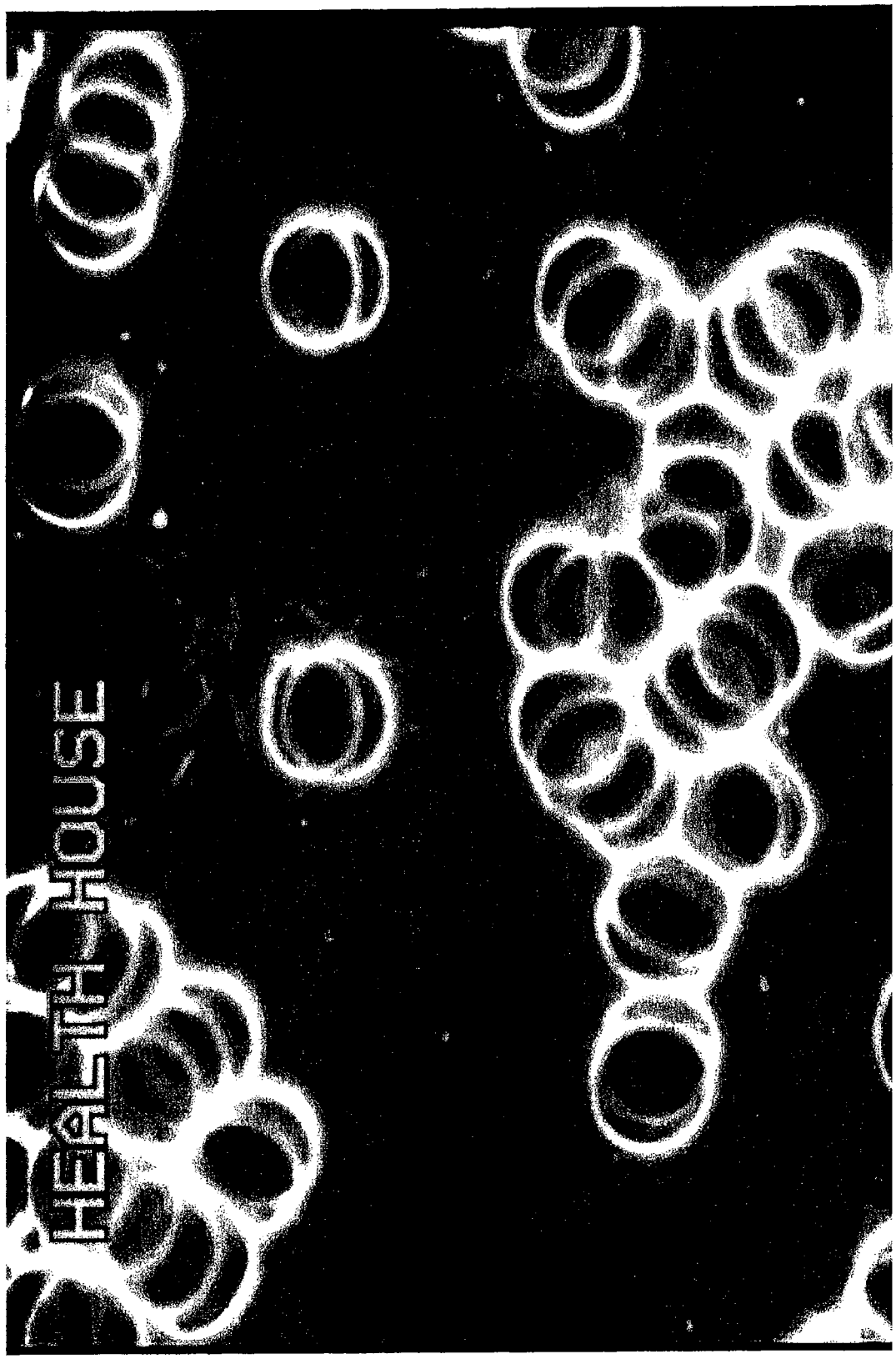
FIG. 5A illustrates the condition of the red blood cells of Subject male 2 before start of study.
Figure 5B:
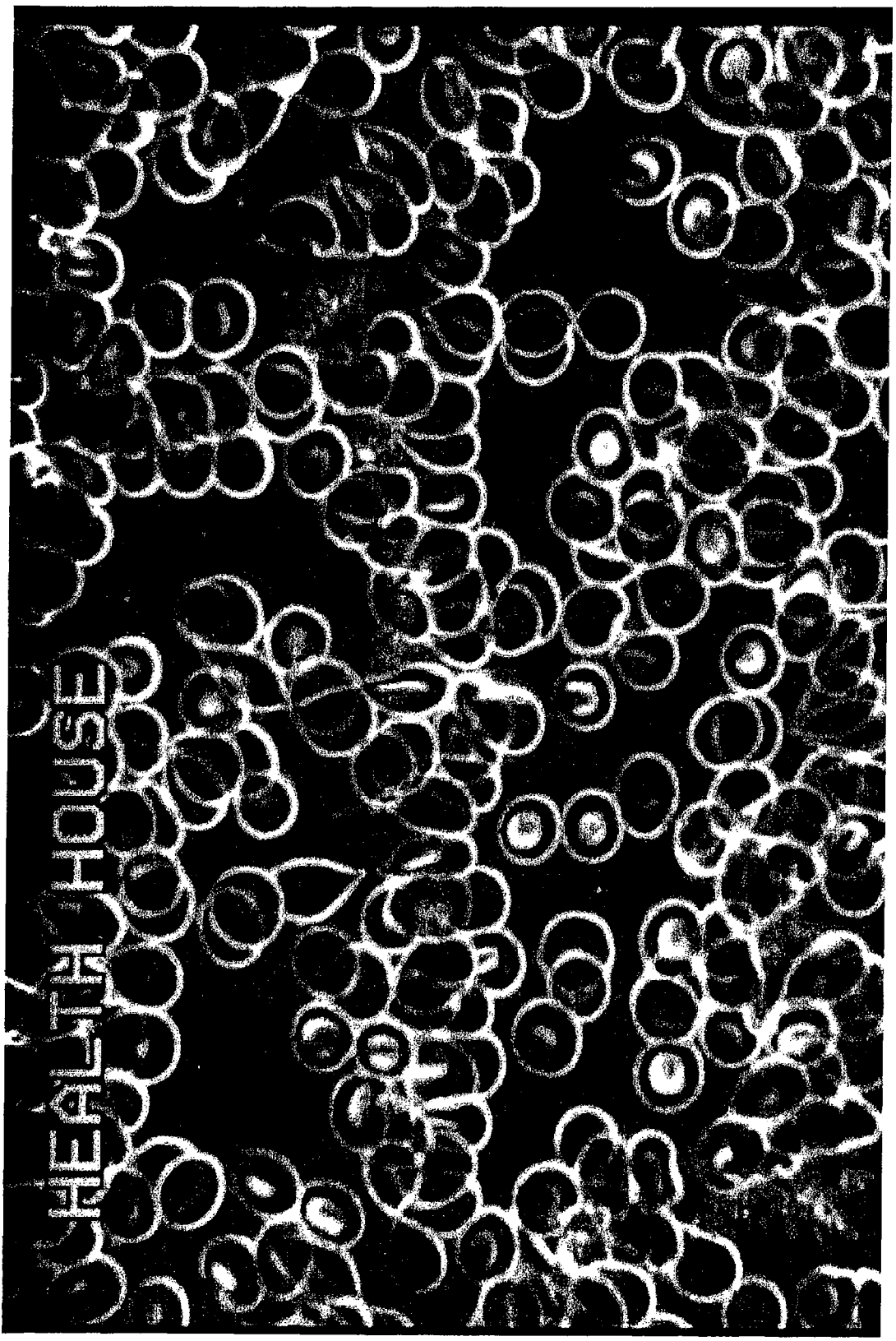
FIG. 5B illustrates the condition of the red blood cells of Subject male 2 after 22 days of administration of product Y.
Figure 5C:
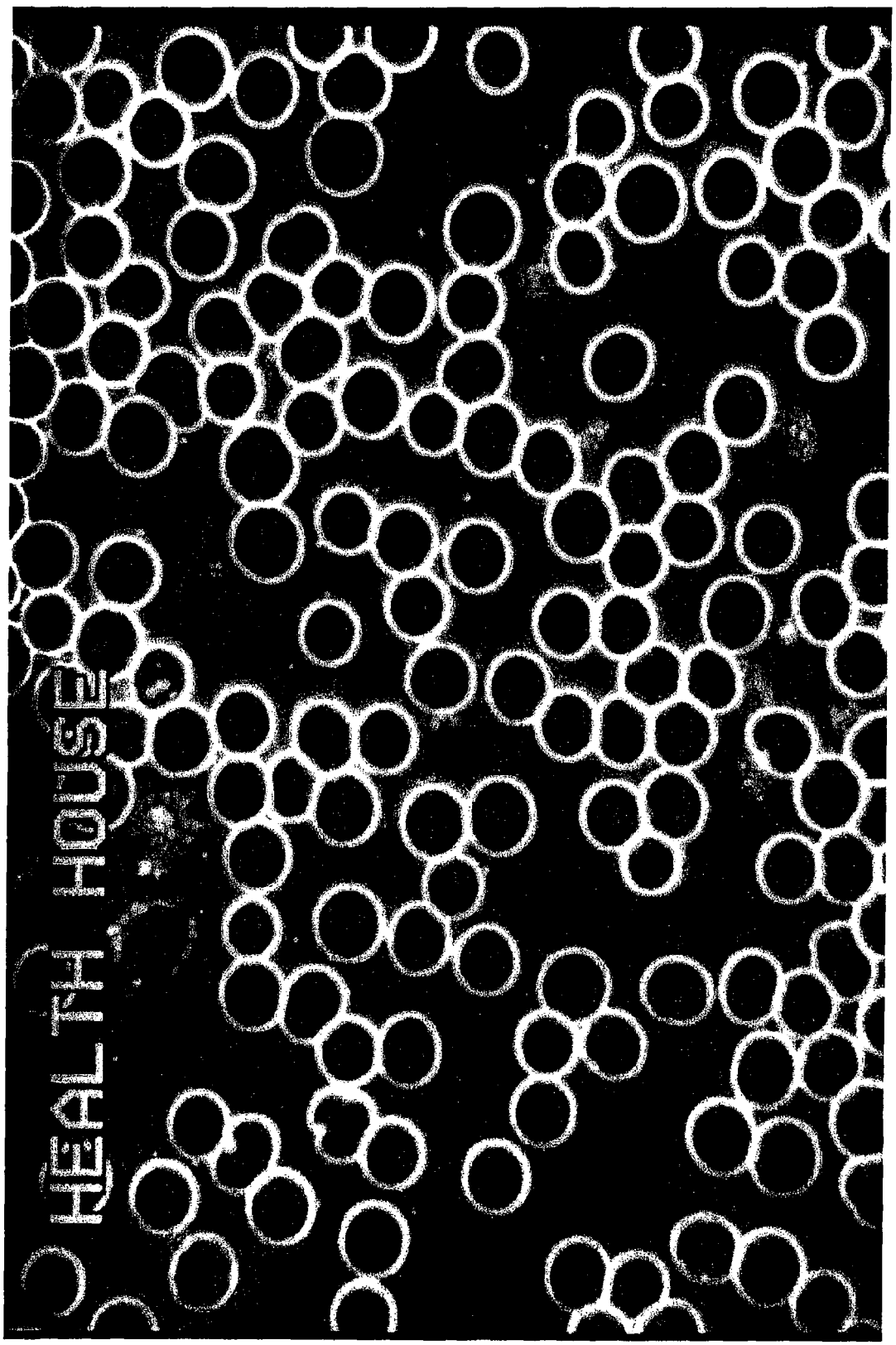
FIG. 5C illustrates the condition of the red blood cells of Subject male 2 after subsequent 22 days of administration of the pharmaceutical composition of Example 1.
Figure 6A:
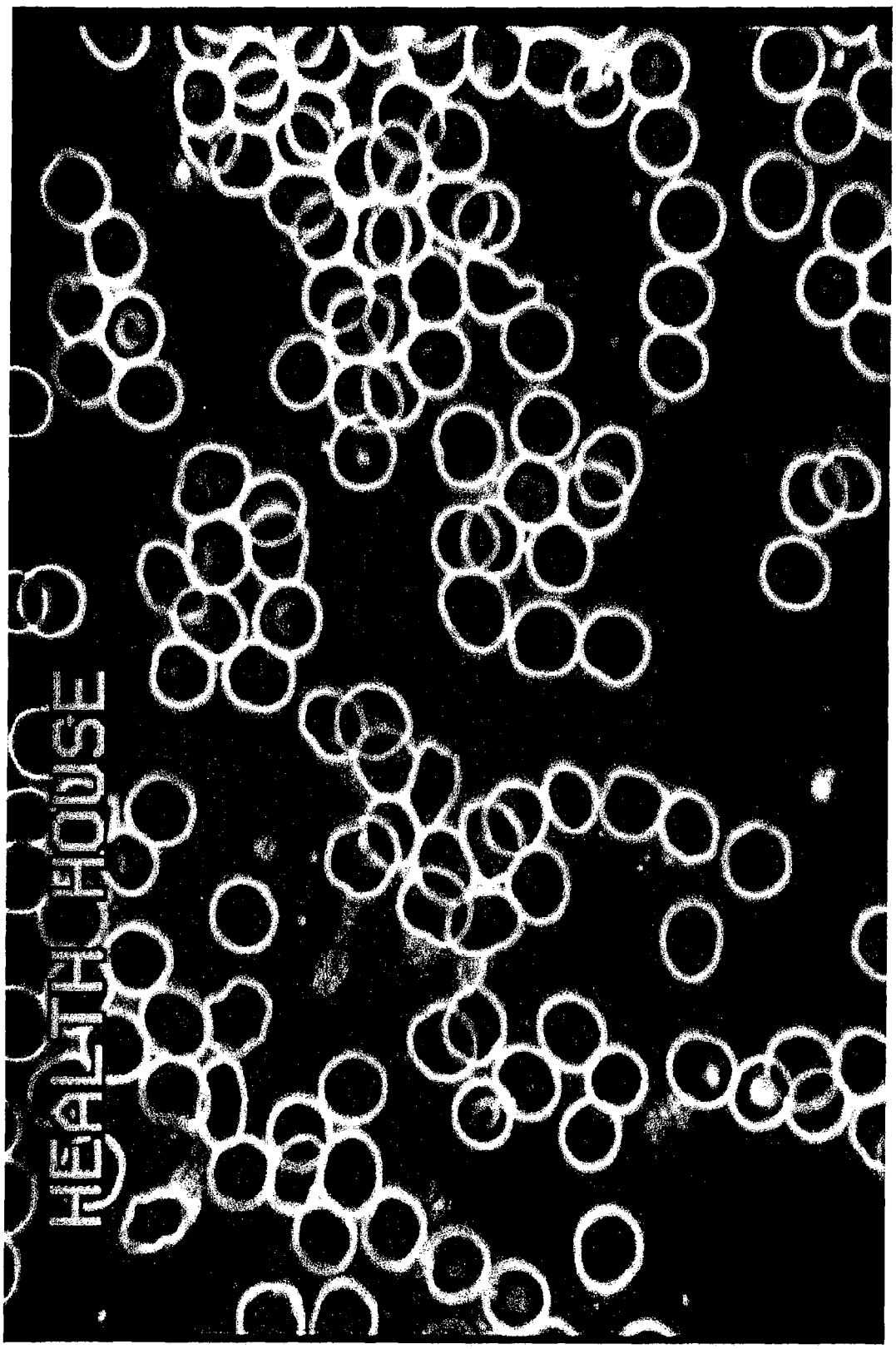
FIG. 6A illustrates the condition of the red blood cells of Subject female 1 before start of study.
Figure 6B:
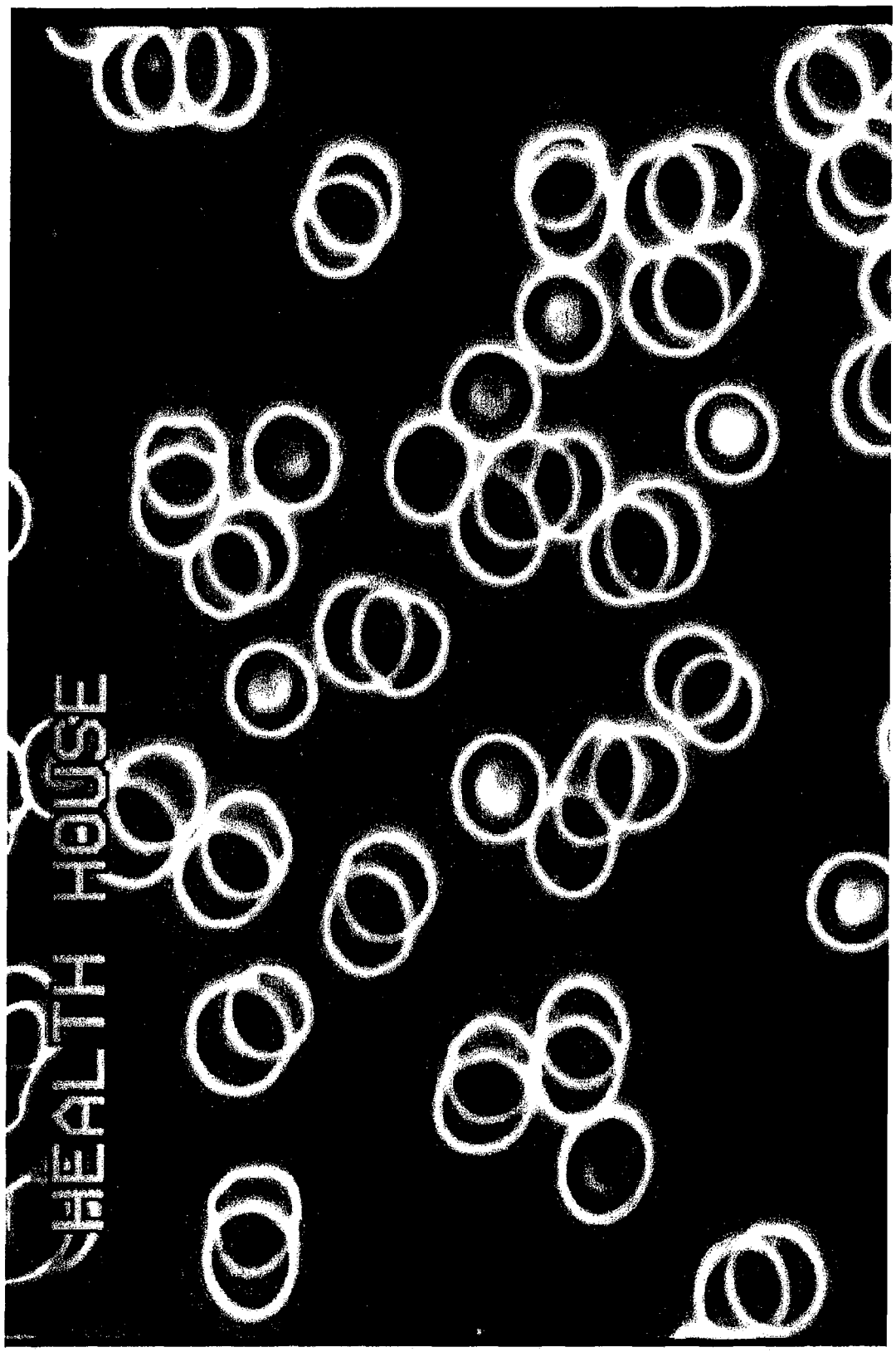
FIG. 6B illustrates the condition of the red blood cells of Subject female 1 after 22 days of administration of product Y.
Figure 6C:
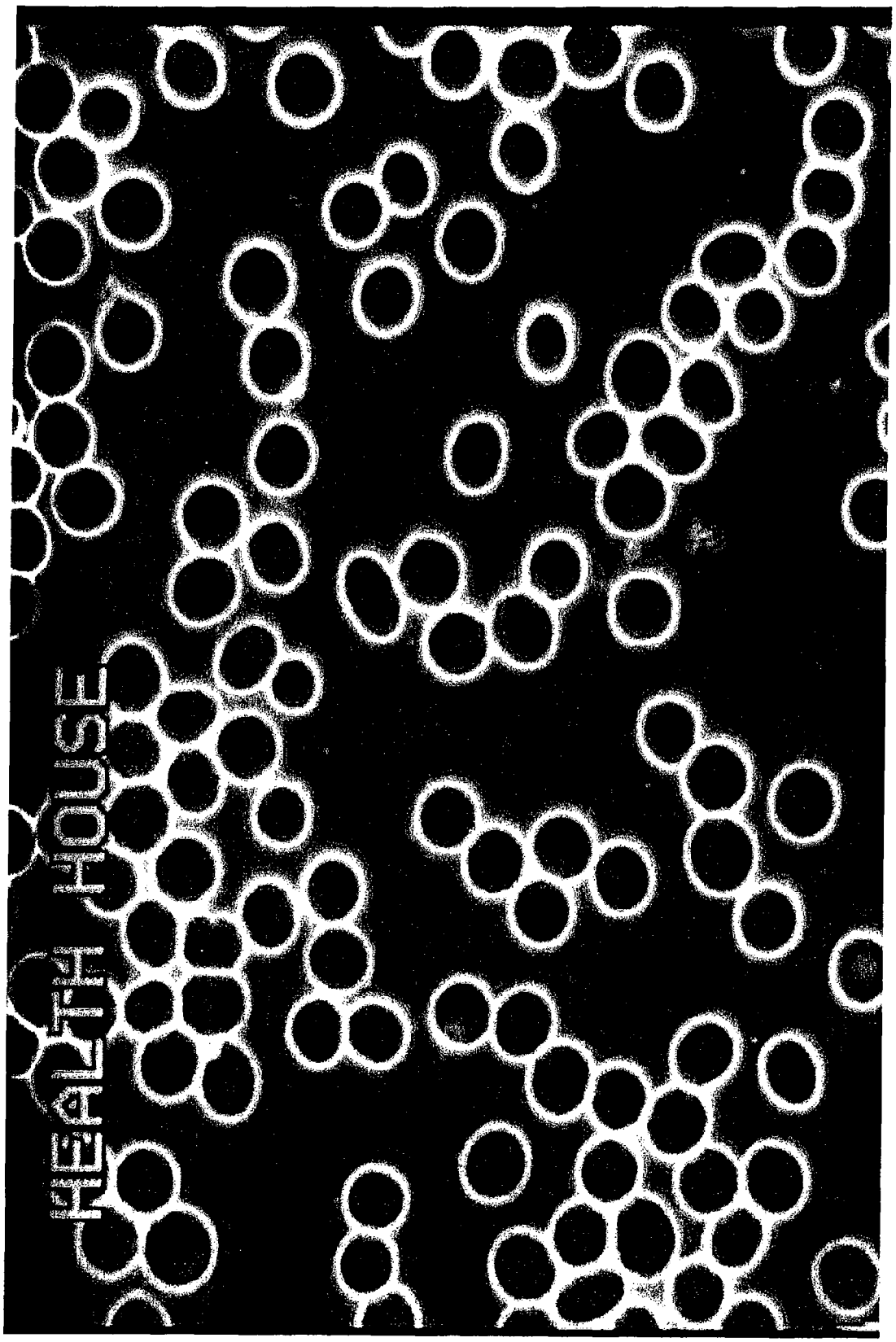
FIG. 6C illustrates the condition of the red blood cells of Subject female 1 after subsequent 22 days of administration of the pharmaceutical composition of Example 1.
Figure 7A:
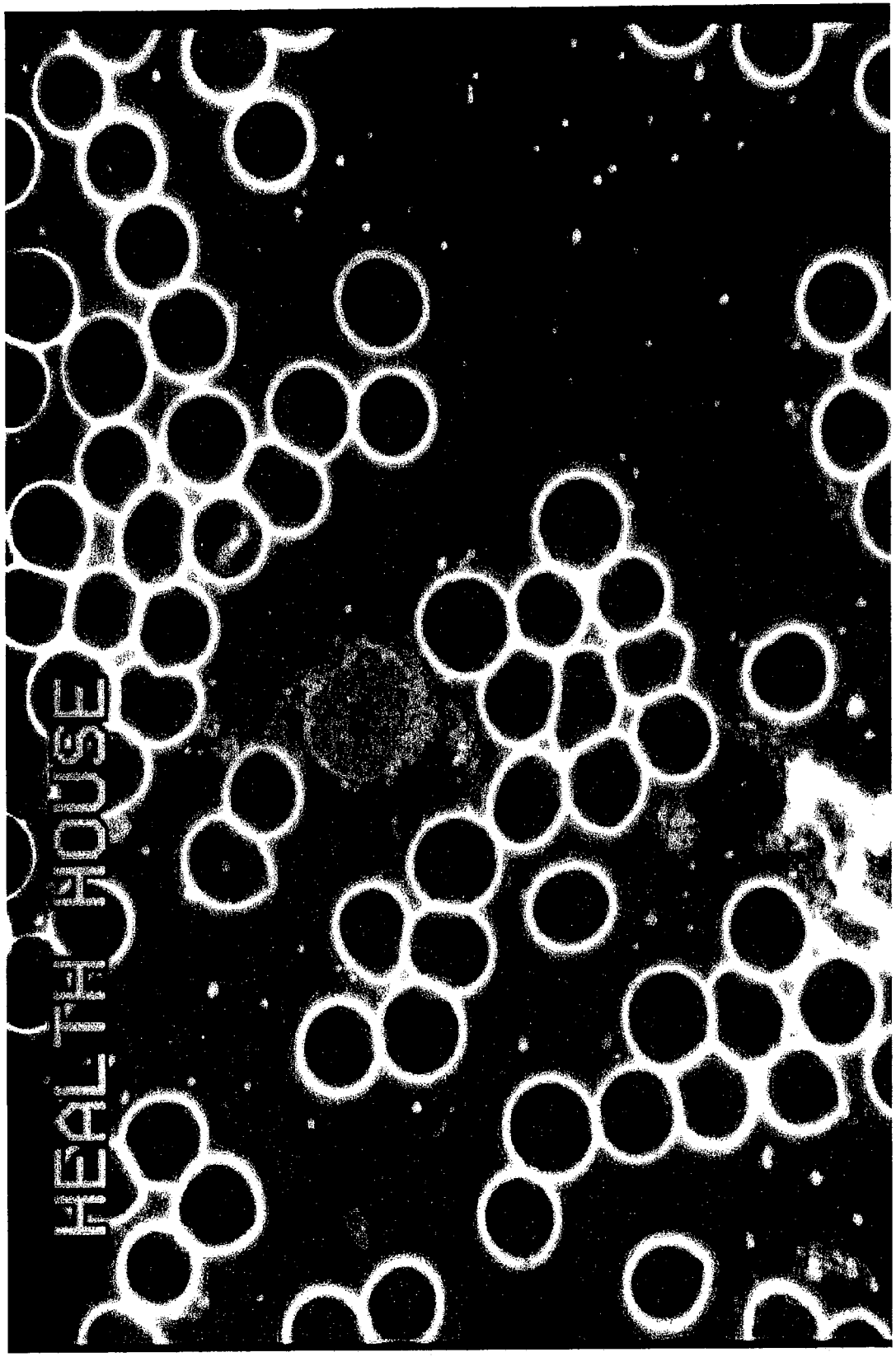
FIG. 7A illustrates the condition of the red blood cells of Subject female 2 before start of study.
Figure 7B:
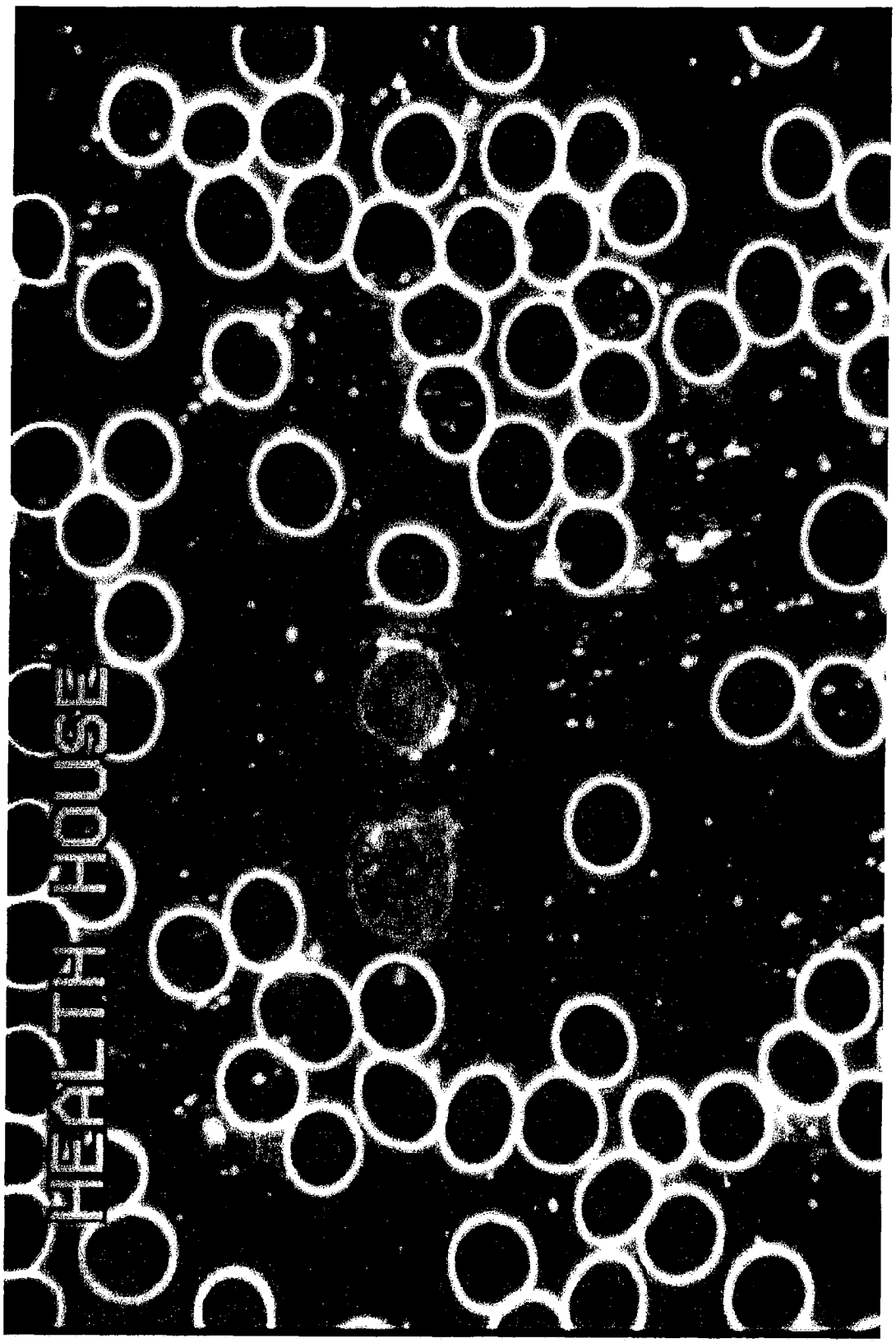
FIG. 7B illustrates the condition of the red blood cells of Subject female 2 after 22 days of administration of product Y.
Figure 7C:
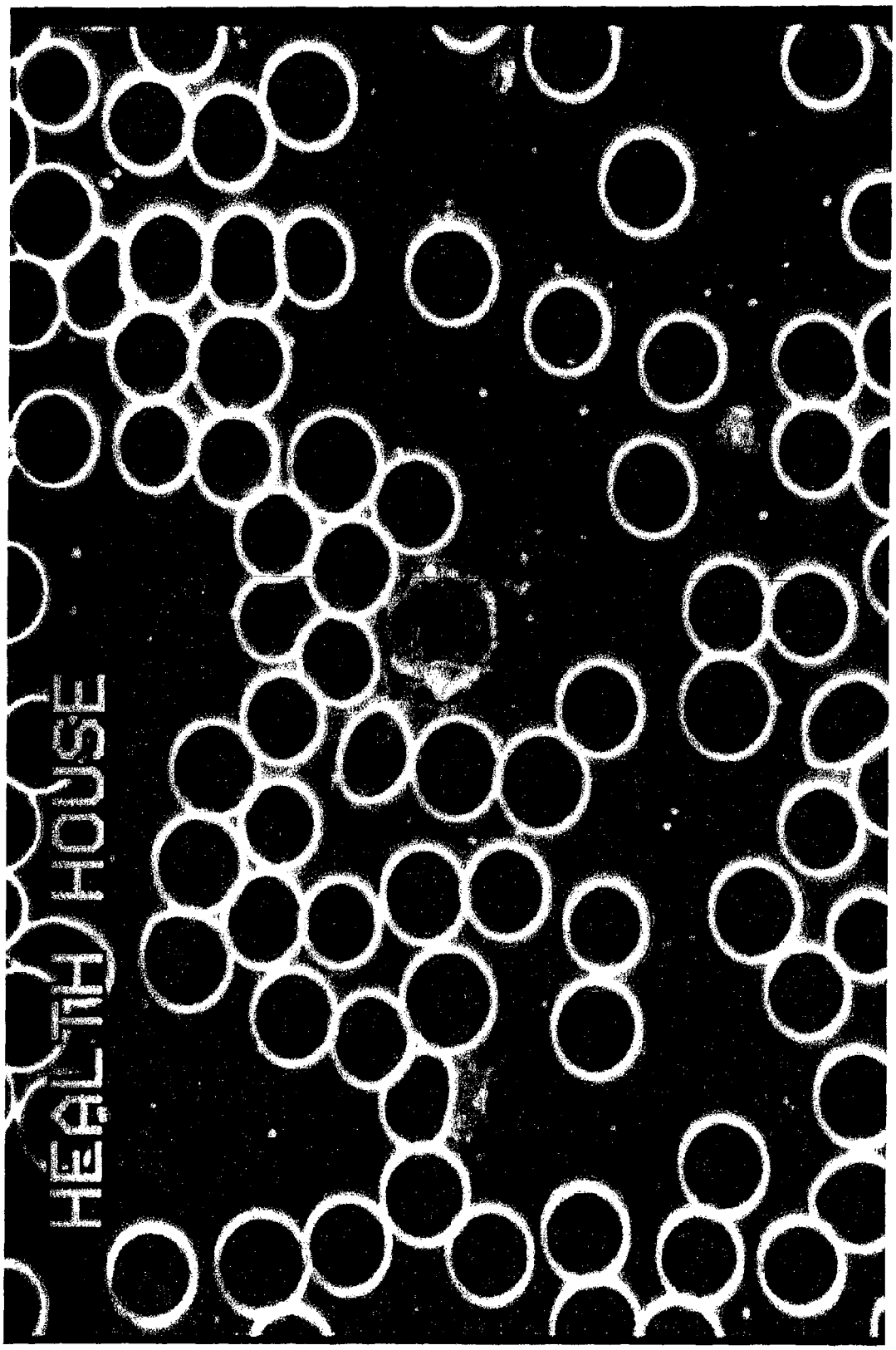
FIG. 7C illustrates the condition of the red blood cells of Subject female 2 after subsequent 22 days of administration of the pharmaceutical composition of Example 1.

Results. The results are presented in Table 1 as well as in FIG. 1A and FIG. 1B (condition of the blood constituents before and after treatment in Subject 1), in FIG. 2 A and FIG. 2 B (condition of the blood constituents before and after treatment in Subject 2) and in FIG. 3 A and FIG. 3 B (condition of the blood constituents before and after treatment in Subject 3). The response of Subject A, B and C to the treatment constitutes direct evidence that the pharmaceutical composition is effective in improving the condition of the blood constituents, by allowing the red blood cells to be more healthy and strong for example, which is an essential condition to the successful oxygenation of the subject's physiological tissues.

TABLE 1

Results of a 30-days treatment of three subjects with the pharmaceutical composition of the present invention

Figure 1:
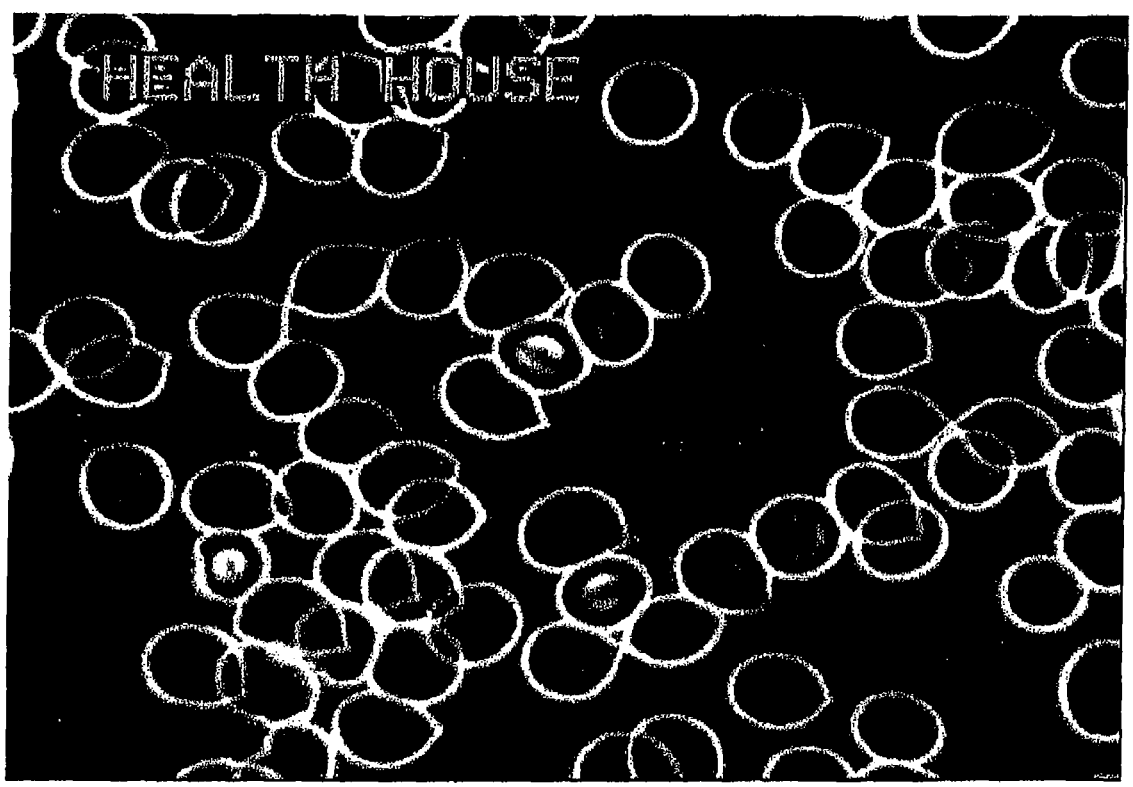
FIG. 1A illustrates the condition of the red blood cells of Subject 1 before start of study.
FIG. 1B illustrates the condition of the red blood cells of Subject 1 after administration of a pharmaceutical composition of Example 1.
Figure 1:
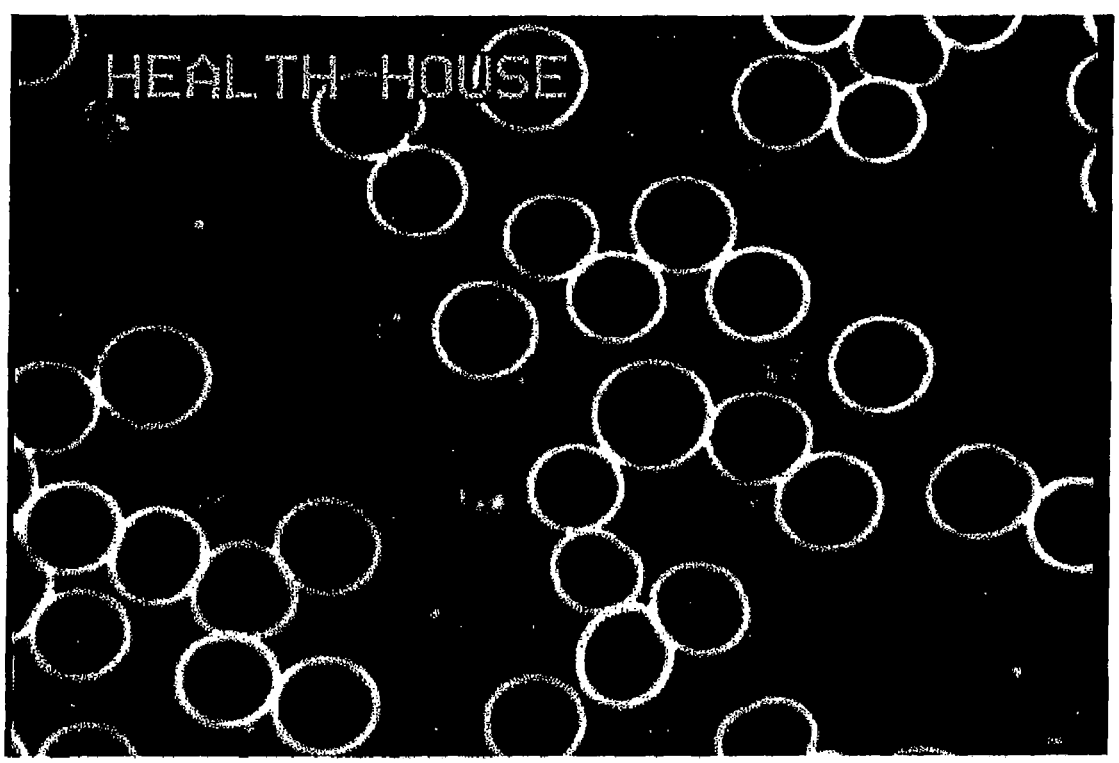

| Subject | Sex | Age | Condition of the blood constituents | |
|---|---|---|---|---|
| | | | Before | After |
| Subject N. 1 | Male | 44 | FIG. 1 A: The red blood cells are misshapen, sticking | FIG. 1 B: The red blood cells are healthy, strong, with no signs |

TABLE 1-continued

Results of a 30-days treatment of three subjects with the pharmaceutical composition of the present invention

| Subject | Sex | Age | Condition of the blood constituents | |
|---|---|---|---|---|
| | | | Before | After |
| | | | together, and showing anemia (indicated by the solid colors in the centre of the red blood cells). | of anemia. They are not sticking together. |
| Subject N. 2 | Female | 87 | FIG. 2 A: The subject's blood shows many red blood cells sticking together and much debris in her blood. | FIG. 2 B: The subject's blood shows remarkable improvement with red blood cells strong and separated from each other and most of the debris gone from her blood. |
| Subject N. 3 | Female | 60 | FIG. 3 A: The subject's blood shows much clumping together of red blood cells and much debris in the blood. | FIG. 3 B: The red cells look strong and healthy, not sticking together, and the debris are gone from her blood. |

EXAMPLE 2

This study compares the action of the 3-herb blend (Energizing Formulation of Example 1) when administered immediately after the 2-herb blend (product Y).

Posology. The subjects were advised not to alter in any other way their regular diet for the time of the treatment. The treatment was carried out on a 44 days basis. During the first 22 days, the subjects each took 5 tablets per day of a product ("Y") containing only Goji fruit and Red Clover blossoms, in the same quantities per tablet as these two ingredients are provided in the Energizing Formulation of Example 1. Each tablet of the "Y" product was made to the same size as the Energizing Formulation product, the difference in volume being made up with an inert filler (di-calcium phosphate).

During the second 22 days of the study, the subjects took the Energizing Formulation of Example 1, 5 tablets per day.

Results. Darkfield Microscopy photos were taken of blood samples at (a) the start of the program (photo #1), (b) at the end of 22 days (photo #2), and (c) at the end of 44 days (photo #3).

Attached are photos from 4 of the subjects (2 male and 2 female) all ranging in age from 31 to 35.

FIGS. 1A, 5A, 6A and 7A show the blood photos at baseline. FIGS. 4A, 5B, 6B and 7B show the blood photos at the end of 22 days on Product Y. FIGS. 4B, 5C, 6C and 7C shows the blood photos at the end of (the subsequent) 22 days on the Energizing Formulation of Example 1.

Each photo were analyzed for the following four criteria: (1) debris in the blood, (2) shape of the red blood cells, (3) collapsed blood cells, as evidenced by cells which appear to have solid centers, and (4) blood cells which stick or clump together.

In each of the four cases shown in FIGS. 4A, 5B, 6B and 7B, there was observable improvement in all four of the above criteria, that is less debris, more round blood cells, fewer collapsed cells, and fewer cells sticking together. Significantly, the greater improvement consistently occurred during the second phase of the study (FIGS. 4B, 5C, 6C and 7C), while subjects were taking the Energizing Formulation of Example 1.

These results indicate that there is a synergy whereby adding Fo-Ti to a blend of Goji fruit and Red Clover (a) produces additional results beyond those achieved by the two herbs alone, and (b) the degree of improvement on the 3-herb blend (Energizing Formulation of Example 1) is greater than achieved by the two herbs alone.

The Energizing Formulation of Example 1 appears to take the subject to a new level of health not achieved by the 2-herb blend.

This phenomenon was further verified by comparing the first half of this study (on Goji and Red Clover) to the study on the Energizing Formulation by itself of Example 1.

In every case, the Energizing Formulation (Example 1) achieved greater results than the Goji/Red Clover combo did in this study.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A premix for the preparation of a pharmaceutical composition, said premix comprising:
    a) dried goji fruit (*Lycium barbarum*) from 20-60% by weight of the premix,
    b) dried red clover blossoms (*Trifolium pratense*) from 10-50% by weight of the premix,
    c) dried Fo Ti (*Polygonum multiflorum* radix) from 5 to 35% by weight of the premix and
    d) organogermanium oxide from 1 to 10% by weight, with respect to the total weight of (a), (b) and (c).

2. The premix according to claim 1, which further comprises, with respect to the total weight of (a), (b) and (c), from 3 to 30% by weight of a glycine precursor.

3. The premix according to claim 2, wherein the glycine precursor is selected from the group consisting of Di-Methyl Glycine, Tri-Methyl Glycine and Magnesium Glycinate.

4. The premix according to claim 1, wherein the organogermanium oxide is selected from the group consisting of beta-carboxyethylgermanium sesquioxide, beta-(alpha-methyl) carboxyethylgermanium sesquioxide and di-(beta-carboxyethyl) germanium hydroxide.

5. A pharmaceutical composition for oxygenating a subject's tissues, said pharmaceutical composition comprising:
    from 40% to 90% by weight of the premix of claim 1 in combination with from 10% to 60% by weight of a pharmaceutically acceptable carrier.

6. The pharmaceutical composition according to claim 5, wherein the premix further comprises, with respect to the total weight of (a), (b) and (c), from 3 to 30% by weight of a glycine precursor.

7. The pharmaceutical composition according to claim 6, wherein said glycine precursor is selected from the group consisting of Di-Methyl Glycine, Tri-Methyl Glycine and Magnesium Glycinate.

8. The pharmaceutical composition according to claim 5, wherein said organogermanium oxide compound is selected from the group consisting of beta-carboxyethylgermanium sesquioxide, beta-(alpha-methyl) carboxyethylgermanium sesquioxide and di-(beta-carboxyethyl) germanium hydroxide.

9. The pharmaceutical composition according to claim 5, wherein said pharmaceutically acceptable carrier is chosen from polyethylene glycol, propylene glycol, propylene glycol monocaprylate, water and mixtures thereof.

10. The pharmaceutical composition according to claim 9, wherein the pharmaceutical composition is in the form of a liquid, a soft-gel capsule, an enteric-coated soft-gel capsule, a capsule or an enteric capsule.

11. The pharmaceutical composition according to claim 5, wherein said pharmaceutically acceptable carrier is selected from the group consisting of sodium lauryl sulfate, methylcellulose, hydroxypropylcellulose, hydroxyethylcellulose, carboxymethylcellulose, polyethylene glycol, polyethylene oxide, polyvinyl alcohols, pregelatinised starch, lactose, mannitol, sucrose, sorbitol, xylitol, polyols, hydroxypropyl methycellulose, polyvinylpyrrolidone, ionic and non-ionic surfactants, polyoxyalkylene derivatives of propylene glycol, organic acids, buffering agents, starch, fillers, lubricants, superdisintegrants, calcium carbonate, calcium phosphate, microcrystalline cellulose, hydrogenated castor oil, glyceryl palmitostearate, talc, stearic acid, vegetable stearate, silica, cross-carmelose sodium and mixtures thereof.

12. The pharmaceutical composition according to claim 11, wherein the pharmaceutical composition is in the form of a pill, a caplet, an enteric-coated caplet, a tablet, an enteric-coated caplet, a lozenge or an enteric-coated lozenge.

* * * * *